United States Patent [19]
Sato et al.

[11] Patent Number: 5,401,741
[45] Date of Patent: Mar. 28, 1995

[54] TOPICAL PREPARATION FOR TREATING OTOPATHY

[75] Inventors: Kiichi Sato, Ishikawa; Akira Handa; Takeji Kitahara, both of Tokyo, all of Japan

[73] Assignee: Daiichi Pharmaceutical Co., Ltd., Tokyo, Japan

[21] Appl. No.: 48,959

[22] Filed: Apr. 12, 1993

Related U.S. Application Data

[63] Continuation of Ser. No. 892,740, Jun. 1, 1992, abandoned, which is a continuation of Ser. No. 622,121, Dec. 6, 1990, abandoned, which is a continuation of Ser. No. 332,913, Apr. 4, 1989, abandoned.

[30] Foreign Application Priority Data

Apr. 8, 1988 [JP] Japan .................................. 63-86378

[51] Int. Cl.⁶ ............................................ A61K 31/535
[52] U.S. Cl. .................................................. 514/230.2
[58] Field of Search ...................................... 514/230.2

[56] References Cited

U.S. PATENT DOCUMENTS 4,382,892  5/1983  Hayakawa et al. ................ 514/233
4,551,456  11/1985  Katz .................................. 514/912

FOREIGN PATENT DOCUMENTS 0274714  7/1988  European Pat. Off. .
0275515  7/1988  European Pat. Off. .

OTHER PUBLICATIONS

English translation of DE 36 32 222 A1 (Jul. 7, 1989).
Infection, vol. 14, Suppl. 4, 1986, pp. S324–S326.
Otol. Fukuoka, vol. 34, No. 4, Jul. 1988, pp. 1028–1034 Abstract Only.
Chemical Abstracts, vol. 110, 1989, p. 29110, abstract 110:29107r.
Chemical Abstracts, vol. 109, 1988, p. 466, abstract 109:156275y.

*Primary Examiner*—Jerome D. Goldberg
*Attorney, Agent, or Firm*—Sughrue, Mion, Zinn, Macpeak & Seas

[57] ABSTRACT

A topical preparation for treating otophathy which contains ofloxacin or a salt thereof as an active ingredient is disclosed.

7 Claims, No Drawings

TOPICAL PREPARATION FOR TREATING OTOPATHY

This is a continuation of application Ser. No. 07/892,740 filed Jun. 1, 1992, now abandoned which is a continuation of application Ser. No. 07/622,121, filed Dec. 6, 1990, now abandoned which is a continuation of prior application Ser. No. 07/332,913, filed on Apr. 4, 1989, now abandoned.

FIELD OF THE INVENTION

This invention relates to a topical preparation for treating otopathy which contains ofloxacin or a salt thereof as an active ingredient.

BACKGROUND OF THE INVENTION

Conventionally employed topical preparations for treating otopathy include solutions containing antibiotics, such as fradiomycin, kanamycin, chloramphenicol, and cefmenoxime.

However, it has been pointed out that these preparations have ototoxicity as side effects or therapeutic effects thereof tend to be decreased due to emergence of resistant microorganisms.

SUMMARY OF THE INVENTION

In order to overcome the above-described problems, the inventors have conducted extensive investigations and, as a result, reached the present invention.

The present invention relates to a topical preparation for treating otopathy which contains ofloxacin or a salt thereof as an active ingredient.

DETAILED DESCRIPTION OF THE INVENTION

The salt of ofloxacin includes acid addition salts formed with organic or inorganic acids, e.g., hydrochloric acid, and salts formed from the carboxyl group and an alkali metal, e.g., sodium and potassium.

The otopathy on which the preparation of the present invention is effective includes inflammatory otopathy, such as otitis media and otitis externa, and particularly purulent otitis media, circumscript external otitis and diffuse external otitis.

Dose forms of the topical preparation of the present invention include sprays, otic solutions, e.g., intratympanic injections and ear drops, ointments, and the like.

The solutions can be prepared by dissolving ofloxacin in water, physiological saline, or an appropriate buffer, adding, if desired, antiseptics, e.g., methyl p-hydroxybenzoate and benzalkonium chloride, to the ofloxacin aqueous solution, and adjusting the solution to a pH in a neutral region. The concentration of ofloxacin in the aqueous solution usually ranges from about 0.05 to about 2% w/v, and preferably from 0.1 to 1% w/v. The ointments can be prepared in a usual manner.

In administration of the ofloxacin solution, several 0.5 ml-doses per day are applied to the external auditory canal by spreading, spraying or instillation, or intratympanically injected through a puncture of the tympanic membrane. The ofloxacin ointment can be applied to the external auditory canal in an adequate dose.

Ofloxacin is of high safety. Acute toxicity ($LD_{50}$) of ofloxacin was found to be 5450 mg/kg (p.o.) in mice, 200 mg/kg or more (p.o.) in dogs, and from 500 to 1,000 mg/kg (p.o.) in monkeys.

The preparation according to the present invention exhibits marked improvements over the conventional drugs in terms of not only ototoxicity but also tissue distribution and excellent therapeutic effects on otopathy, particularly otitis media and otitis externa. Accordingly, the preparation of the present invention is useful as a topical preparation for treating otopathy.

The present invention is now illustrated in greater detail with reference to the following Examples and Test Examples, but the present invention is not deemed to be limited thereto.

EXAMPLE 1

Ofloxacin was dissolved in distilled water for injection, and the solution was adjusted to a pH of from 6.0 to 7.0, followed by bactericidal filtration to prepare a 0.5% ofloxacin aqueous solution.

EXAMPLE 2

Ofloxacin was dissolved in physiological saline, and the solution was treated in the same manner as in Example 1 to prepare an ofloxacin solution.

EXAMPLE 3

Ofloxacin was dissolved in physiological saline, and the solution was treated in the same manner as in Example 1 to prepare a 0.3% ofloxacin aqueous solution.

Test Example 1

1) Test Method:

Fifteen white guinea pigs were divided into the following two groups: 10 in an ofloxacin group topically administered with a 0.3% ofloxacin solution (hereinafter referred to as "0.3% OFLX group") and 5 in a control group administered with physiological saline.

Before testing, the auditory brain-stem response (hereinafter referred to as "ABR") of each animal was determined to obtain a response threshold. A Logon sound wave having a frequency of 10,000 was used as a stimulating sound.

The left tympanic membrane was punctured under general anesthesia, and 0.2 ml of the ofloxacin solution of Example 3 or 0.2 ml of the control solution (physiological saline) was injected into the tympanic cavity once a day for consecutive 7 days. ABR was measured after 10 days from the final day of injection.

2) Result:

The change between the ABR threshold before the administration and that after the administration was shown in Table 1 below.

TABLE 1

| | Change of ABR Threshold Threshold (dB, Mean ± S.E.) | |
|---|---|---|
| | Before Admin. | After Admin. |
| 0.3% OFLX Group | 30 ± 1.3 | 34.5 ± 1.4 |
| Control Group | 30 ± 1.6 | 35 ± 1.6 |

As is apparent from Table 1, the threshold changes in both of the 0.3% OFLX group and the control group were slight (4.5 dB and 5.0 dB, respectively), indicating that the reduction of acoustic acuity due to the administration of ofloxacin was negligible.

Test Example 2

1) Test Animal and Administration Route:

Twenty-nine guinea pigs showing normal Preyer's reflex (body weight: 250 to 350 g) were divided into the following three groups; 12 in a group receiving topical administration of 0.5% ofloxacin solution (hereinafter referred to as "0.5% OFLX group"); 13 in a group topically administered with gentamicin (hereinafter referred to as "GM group"); and 4 in a control group administered with physiological saline.

After ketalar and a muscle relaxant (xylazine) were intramuscularly administered, an incision of 2 mm in diameter was made at the middle ear from the posterior portion of the ear of the guinea pig, and a tube of the same diameter was inserted into the tympanic cavity through the opening and sealed and fixed with an adhesive. The incision wound was temporarily sutured and closed. Immediately after the operation, ABR was recorded. From the same day, 0.2 ml of a 4% gentamicin solution, 0.2 ml of the ofloxacin solution of Example 2, or 0.2 ml of the control solution (physiological saline) was injected through the tube into the tympanic cavity. The injection was made once a day for consecutive 10 days. On the 10th day, ABR was again recorded, and the animals were killed.

2) Method of Observation:

i) Measurement of ABR:

An ear drum lead was used for the measurement of ABR. The ground electrode was placed on the foreleg of the same side as the injected ear of the guinea pigs. A clicking sound was given to the external auditory canal from a tube via a crystal receiver. The auditory response was given as a reaction wave, and an average of 200 measurements obtained by a computer was recorded by an XY recorder. The ABR threshold in the individual animal was obtained from the resulting electrocochleogram.

ii) Morphological Observation a. Microscopic Observation:

A sample tissue (middle ear mucosa) was fixed in formalin using the auditory bulla in a conventional method. After decalcification, the sample was embedded in paraffin and sliced. The paraffin section was stained with hematoxylin and eosin and microscopically observed.

b. Scanning Electron microscopic (SEM) Observation:

A sample tissue (cochlea) was thoroughly washed in a jet stream of physiological saline and fixed in a 2.5% glutaraldehyde solution for 12 hours using a conventional method. Then, the tissue was again washed with a phosphate buffer solution (pH 7.4) by shaking, fixed in a 1% osmic acid solution for 1 hour, and electrically stained with osmium tannate. The tissue was dehyrated with an alcohol using a conventional method and dried at a critical point, followed by sputtering with platinum ions. The sample thus prepared was observed under a Hitachi S-570 Model scanning electron microscope.

iii) Determination of Distribution of Ofloxacin

Distribution of the drug to the serum, brain tissue, middle ear mucosa, and cochlear perilymph was examined in the control group and the 0.5% OFLX group. A blood sample was collected from the carotid artery, and the brain tissue was excised immediately after decapitation. The middle ear mucosa was stripped off after thorough washing of the middle ear cavity with physiological saline. Thereafter, the cochlear perilymph was collected by a glass capillary.

The concentration of the drug in the tissue was biologically assayed according to a paper disc method using *B. subtilis* ATCC 6051 and *Ecoli* Kp as test microorganisms.

The serum was used as untreated for the test. The brain tissue was homogenized together with an equal weight of a 0.1M phosphate buffer solution (pH 7.0) in a glass-made homogenizer to prepare a 50% homogenate solution.

Sampling of the perilymph and the middle ear mucosa was carried out within the same time zone, and the samples were pooled in the cold. After measuring the volume of the perilymph the sample was ten-fold diluted with a phosphate buffer and tested. On the other hand, after weighing and homogenizing, the mucosa sample was tested.

3) Result:

i) Change of Acoustic Acuity:

The change of ABR thresholds are shown in Table 2 below.

TABLE 2

| ABR Threshold Change | |
|---|---|
| | Threshold Change (dB, Mean ± S.E.) |
| 0.5% OFLX Group | −7.9 ± 2.8** |
| GM Group | −38.5 ± 5.8* |
| Control Group | −15.0 ± 5.8 |

Note:
**$P < 0.01$ vs. GM group
*$P < 0.05$ vs. control group

As can be seen from Table 2, a reduction of acoustic acuity of an average of 15 dB was noted in the control group, while the GM group showed a rise in ABR threshold of 38.5 dB, that is, a remarkable reduction of acoustic acuity. On the other hand, the 0.5% OFLX group showed an extremely small rise in ABR threshold, i.e., a reduction in auditory acuity, averaging 7.9 dB. Therefore, it was confirmed that ofloxacin did not have any ototoxicity.

ii) SEM Observations on Cochlear Hair Cell:

The SEM picture of the cochlea in the control group or 0.5% OFLX group revealed that the hair of the outer and inner hair cells at the basal turn and the second or third turns suffered from no disturbance.

On the other hand, the SEM picture of the cochlea of the GM group revealed that the outer and inner hair cells suffered from disturbance of the row of the hair cells or disappearance of the hair cells from the basal turn through the third turn. There was observed a tendency that the disturbance of the inner hair cells became serious toward the upward turn. On the other hand, the outer hair cells did not show such a tendency, however, a stronger disturbance of the outer hair cells was noted at the third turn thereof. Also, when SEM was also carried out on 6 ears on the opposite side of the animals of the GM group, a slight disturbance of the outer hair cells was observed in every case, in spite of the fact that GM was not administered directly to these ears.

iii) Observations of Middle Ear Mucosa:

Considerable inflammation, such as remarkable cellular infiltrate in the mucosa or thickening of the mucous periosteum, were observed in the control group. To the contrary, such inflammation was not observed in the middle ear mucosa of the 0.5% OFLX group and the GM group.

iv) Distribution of Ofloxacin:

The results are shown in Table 3.

TABLE 3

Concentration of OFLX in Various Tissues After OFLX Admin.

| | No. | Time from Admin. (hr) | Ofloxacin Concen. ($\mu$g/ml or $\mu$g/g) | | | |
|---|---|---|---|---|---|---|
| | | | Serum | Brain | Mid. Ear Mucosa | Lymph |
| OFLX Group | 1 | 1–1.5 | <0.19 | <0.20 | 78.70 | <1.00 |
| | 2 | " | 0.91 | <0.20 | | |
| | 3 | " | <0.19 | <0.20 | | |
| | 4 | " | <0.19 | <0.20 | | |
| | 5 | 1.5–2 | <0.19 | <0.20 | 45.85 | 3.80 |
| | 7 | " | 1.20 | <0.20 | | |
| | 9 | " | <0.19 | <0.20 | | |
| | 10 | " | <0.19 | <0.20 | | |
| | 6 | 2–2.5 | <0.19 | <0.20 | 40.85 | <1.00 |
| | 11 | " | <0.19 | <0.20 | | |
| | 12 | " | 0.19 | <0.20 | | |
| | 13 | " | 0.39 | <0.20 | | |
| Control Group | 1 | | | <0.20 | | |
| | 2 | | | <0.20 | | |

As can be seen from Table 3, the ofloxacin concentration in the serum was less than 0.19 μg/ml in most of the cases of the OFLX group. Therefore, ofloxacin did not distribute to tissues other than the middle ear. In particular, this can be seen from the fact that the concentration of ofloxacin in the brain was less than 0.20 μg/g in all cases, the same level in the controls. Therefore, it was considered that side effects on the central nervous system, which are liable to be induced by the use of new quinolone-type antibacterial agents, were not involved at all in the case of administration of ofloxacin to the ear. On the other hand, distribution of ofloxacin to the middle ear mucosa, which is of the most importance from the standpoint of effectiveness, was higher than 40 μg/g.

As above demonstrated, ofloxacin, when topically administered into the ear, caused substantially no ototoxicity and exhibited excellent distribution to the desired middle ear mucosa without showing substantially any distribution to tissues, particularly to the brain, other than the desired tissues. Thus, the ofloxacin topical preparations for otopathy according to the present invention are believed to be of extremely high clinical use.

Test Example 3

It is known that otitis media and otitis externa are induced through bacterial infection. Hence, the antibacterial activities of ofloxacin on all the bacteria isolated from the lesion of a patient suffering from purulent otitis media were assayed in comparison with other drugs for otopathy. The results obtained are shown in Table 4 below.

TABLE 4

$MIC_{80}$ on Test Microorganisms

| Drug | $MIC_{80}$ ($\mu$g/ml) | Total Number of Strains | Composition of Microorgansims (%) | | | | |
|---|---|---|---|---|---|---|---|
| | | | S. aureaus | S. epidermidis | P. aeruginosa | Proteus | Other Microorganisms |
| Ofloxacin | 1.56 | 174 | 33.3 | 11.3 | 14.5 | 11.1 | S.pneumoniae Corynebacterium anaerobic bacteria Streptococcus A. calcaeticus Peptostreptococcus |
| Cefmenoxime | 25 | 237 | 37.7 | 10.77 | 13.5 | 13.1 | |
| Chloramphenicol | 50 | 237 | | | | | |
| Fradiomycin | 100 | 237 | | | | | |

As is apparent from Table 4 above, ofloxacin exhibited more excellent antibacterial activities on bacteria causing purulent otitis media than other conventional drugs.

While the invention has been described in detail and with reference to specific embodiments thereof, it will be apparent to one skilled in the art that various changes and modifications can be made therein without departing from the spirit and scope thereof.

What is claimed is:

1. A method for treating otopathy which comprises the topical otic administration of an amount of ofloxacin or a salt thereof effective to treat otopathy in a pharmaceutically acceptable carrier to the area affected with otopathy.

2. The method of claim 1 wherein said otopathy is otitis media.

3. The method of claim 2 wherein said otopathy is otitis externa.

4. The method of claim 2 wherein the concentration of ofloxacin in the pharmaceutically acceptable carrier is about 0.05 to about 2% w/v.

5. The method as claimed in claim 4, wherein the dosage form of ofloxacin is an aqueous solution.

6. The method as claimed in claim 5, wherein the aqueous solution of ofloxacin is applied to the external auditory canal by instillation.

7. The method as claimed in claim 6, wherein the aqueous solution of ofloxacin is intratympanically injected through a puncture of the tympanic membrane.

* * * * *